US009918633B2

(12) United States Patent
Lipari

(10) Patent No.: US 9,918,633 B2
(45) Date of Patent: Mar. 20, 2018

(54) APPARATUS AND METHOD FOR DETERMINING THE ORIENTATION OF ANATOMICAL CORNEA STRUCTURES

(71) Applicant: PHRONEMA S.R.L., Bari (IT)

(72) Inventor: Eugenio Lipari, Bari (IT)

(73) Assignee: PHRONEMA S.R.L., Bari (IT)

( * ) Notice: Subject to any disclaimer, the term of this patent is extended or adjusted under 35 U.S.C. 154(b) by 6 days.

(21) Appl. No.: 14/907,490

(22) PCT Filed: Jul. 28, 2014

(86) PCT No.: PCT/IB2014/063482
§ 371 (c)(1),
(2) Date: Jan. 25, 2016

(87) PCT Pub. No.: WO2015/011692
PCT Pub. Date: Jan. 29, 2015

(65) Prior Publication Data
US 2016/0183787 A1     Jun. 30, 2016

(30) Foreign Application Priority Data

Jul. 26, 2013  (IT) .............................. MI2013A1262

(51) Int. Cl.
*A61B 3/14*     (2006.01)
*A61B 3/00*     (2006.01)
*A61B 3/107*    (2006.01)
*G02B 27/28*    (2006.01)
*A61F 9/013*    (2006.01)

(52) U.S. Cl.
CPC .............. *A61B 3/14* (2013.01); *A61B 3/0025* (2013.01); *A61B 3/107* (2013.01); *G02B 27/281* (2013.01); *A61F 9/013* (2013.01)

(58) Field of Classification Search
CPC ........ A61B 3/14; A61B 3/0025; G02B 27/281
USPC .................................................. 351/206, 246
See application file for complete search history.

(56) References Cited

U.S. PATENT DOCUMENTS 7,967,440 B1    6/2011  Copland

FOREIGN PATENT DOCUMENTS

JP     2004236982    8/2004
WO     99/62397      12/1999

OTHER PUBLICATIONS

International Searching Authority, International Search Report and Written Opinion, PCT/IB2014/063482, dated Nov. 6, 2014.

*Primary Examiner* — Jack Dinh
(74) *Attorney, Agent, or Firm* — Greer, Burns & Crain, Ltd.

(57) ABSTRACT

An apparatus for determining an orientation of anatomical cornea structures includes: a lighting device, configured to direct a first luminous radiation, polarized with an orientable polarization direction, towards a cornea, when the cornea is in an observation seat; a control device, configured to modify an orientation of the polarization direction; an image acquisition device, arranged so as to receive a second luminous radiation, transmitted through the cornea arranged in the observation seat and illuminated by the first luminous radiation; and an acquisition polarizing filter, arranged so as to intercept the second luminous radiation directed towards the image acquisition device.

22 Claims, 4 Drawing Sheets

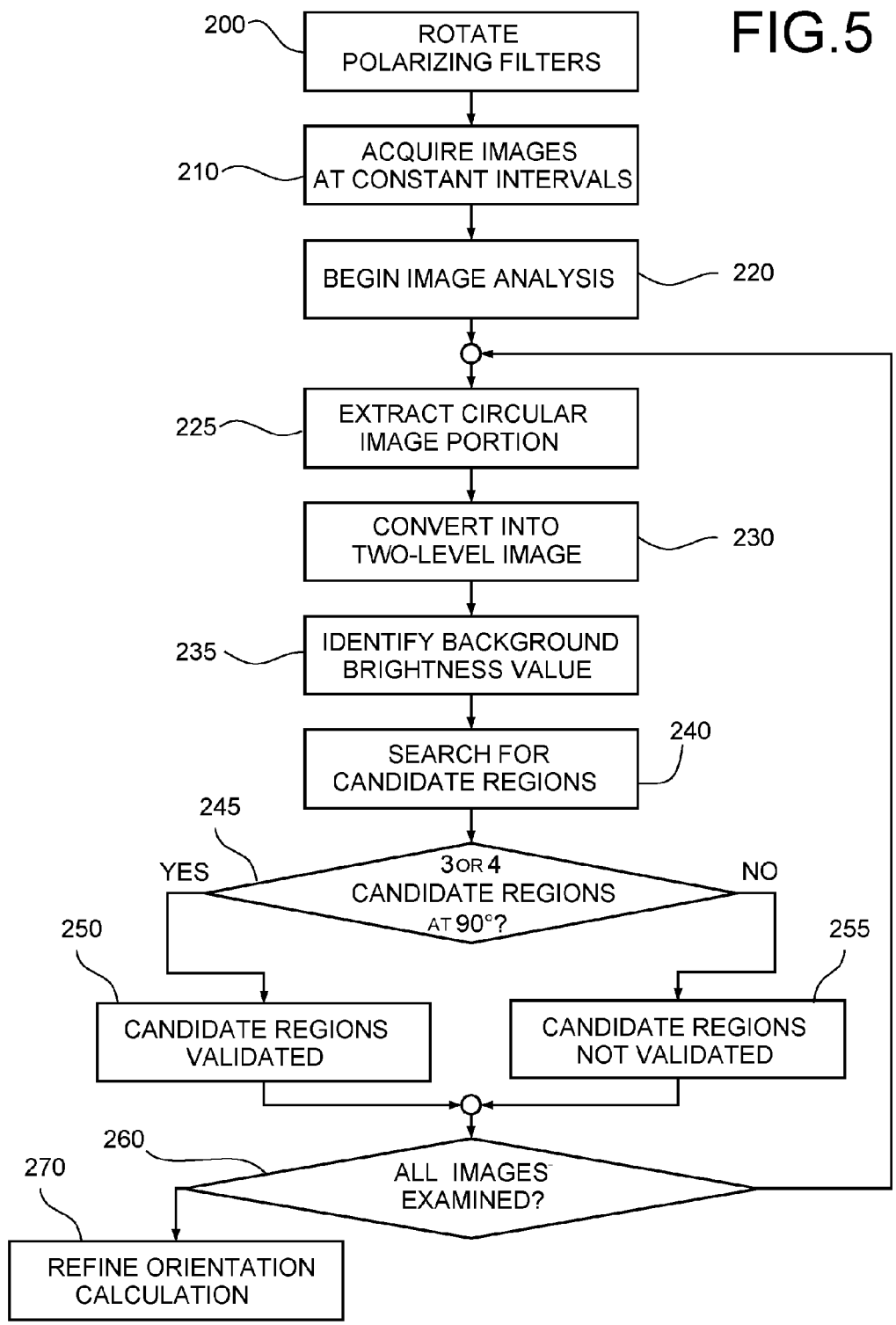

APPARATUS AND METHOD FOR DETERMINING THE ORIENTATION OF ANATOMICAL CORNEA STRUCTURES

This application is a U.S. National Stage under 35 U.S.C. § 371 of International Application No. PCT/IB2014/063482, filed Jul. 28, 2014, which claims priority to Italian application No. MI2013A001262 filed Jul. 26, 2013.

TECHNICAL FIELD

The present invention relates to an apparatus and a method for determining the orientation of anatomical cornea structures.

BACKGROUND ART

In ophthalmic surgery, two different techniques are known for cornea transplants.

Penetrating (or full-thickness) transplants entail removal of the entire thickness of the patient's corneal tissue and complete replacement with a donor cornea. By an appropriate device, a circular portion of the recipient patient's central cornea is removed by complete penetration. The tissue removed is fully replaced by a lenticle of equivalent geometry, obtained from the donor cornea. The operation concludes with suture (with different techniques possible) around the perimeter of the transplanted tissue. Following a penetrating transplant, the patient uses only the donor portion of cornea for vision.

In the case of lamellar transplants, on the other hand, only a certain thickness of corneal tissue is removed from the epithelial layer and/or from the endothelial layer of the recipient patient, using one of several surgical techniques available. Lamellar transplants are classified, according to the residual thickness of the recipient tissue, as DALK (Deep Anterior Lamellar Keratoplasty) if the removal is deep and the residual tissue thickness of the recipient is modest, and ALK (Anterior Lamellar Keratoplasty) if the removal is more superficial and the residual tissue thickness is greater. Lamellar transplants also comprise endothelial transplants. In this case the corneal lamella of the donor refers to the rear portion of stroma on which the endothelial cells are arranged.

The removal of material allows a seat to be obtained, normally called receiver stromal bed or more simply receiver bed, in the patient's stromal tissue. The receiver stromal bed is shaped to receive a lenticle or stromal flap from a donor.

Regardless of the surgical technique adopted for preparation of the receiver bed, the grafting of the donor stromal flap creates an interface between the tissue of the recipient and the tissue of the donor. The interface influences the properties of the resulting optical system.

In a significant number of cases, a cornea transplant, whether lamellar (anterior or posterior) or penetrating, although correctly performed, does not give the patient the expected refractive results in terms of improvement of the quality of vision. In particular, and this is not uncommon, evaluation of the transplant performed by the usual objective ophthalmic instrumental examinations may not correspond to the subjective perception of the patient, who does not notice the predicted improvements. Post-operative examinations show that, at times, the quality of vision is not satisfactory even when both the receiver structure and the donor flap are perfectly transparent according to the traditional ophthalmic examination procedures. It has further been found that the visual result is all the more predictable the greater the quantity of tissue removed from the cornea of the recipient and in the case of endothelial transplants, the thinner the stromal lamella of the donor.

Especially in the case of lamellar transplants, the properties of the final optical system are therefore determined not only by the quality of the residual receiver tissue and the donor tissue, but also by the way in which the donor flap is coupled to the receiver bed. However, analogous problems have been encountered also in the case of penetrating transplants.

The problem of determining the correct orientation of the donor cornea is therefore of a general nature, even if perceived more acutely in the case of lamellar transplants.

DISCLOSURE OF INVENTION

The object of the present invention is to provide an apparatus and a method for determining an orientation of anatomical cornea structures, which allow the limitations described to be overcome and, in particular, allow improvement of the cornea transplant procedures and the quality of vision after cornea transplant.

According to the present invention an apparatus and a method are provided for determining the orientation of anatomical cornea structures, as defined in claims 1 and 12 respectively.

BRIEF DESCRIPTION OF THE DRAWINGS

For a better understanding of the invention, some embodiments thereof will now be described, purely by way of non-limiting example and with reference to the accompanying drawings, in which:

FIG. 5 is a flow diagram relative to further phases of the method of FIG. 4;

BEST MODE FOR CARRYING OUT THE INVENTION

The invention is based on observation of the structure of a human cornea.

The stroma occupies approximately 90% of the thickness of the human cornea and is composed mainly of collagen, which forms fibrils of approximately 25-30 nm in diameter. The fibrils are organised in fasciae or wider fibres called corneal lamellae. In each lamella, the collagen fibrils are immersed in a matrix rich in proteoglycans, glycoproteins, mineral salts and keratocytes and are arranged parallel to one another.

Figure 1:
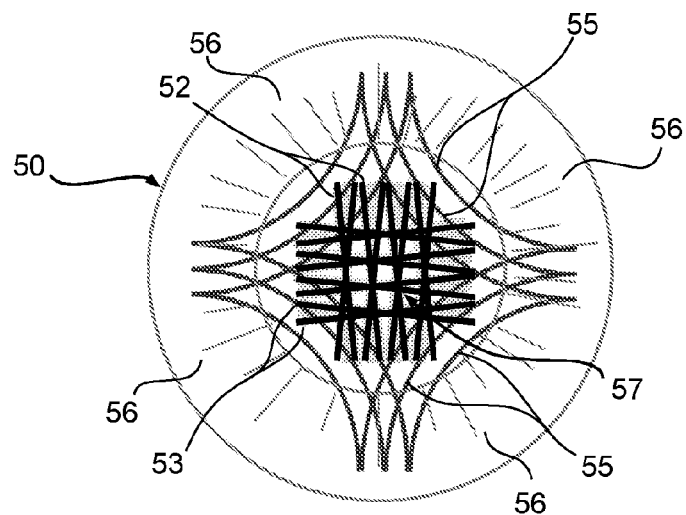
FIG. 1 is a frontal view of a cornea.

The corneal lamellae of the deepest layers (belonging to the lower two thirds) of the stroma are not organised isotropically, but have a preferential orientation along the superoinferior or nasal-temporal corneal meridians (therefore along one of two substantially perpendicular directions)

and form a matrix. In FIG. 1, which illustrates a cornea 50, the perpendicular lamellae are shown schematically and are indicated by the numbers 52 and 53.

In portions of deep stroma, but in more peripheral areas, the lamellae are distributed along curved lines which form arcs 55 defining four rounded regions or lobes 56, separated by a central cruciate region 57. The ends of the cruciate region 57 lie near the insertions of some of the main oculomotor muscles, in particular the superior, inferior, lateral and medial rectus muscles. The lamellae of this type have a distribution such as to produce substantially isotropic scattering effects in optical terms and are laid over the deep corneal lamellae 52, 53, which are organised in a matrix in substantially perpendicular directions.

In the case of lamellar cornea transplants, the corneal flap explanted from the donor contains a large part of deep tissue, organised anisotropically. If the donor tissue is grafted with random orientation, the optical interaction with the receiver bed cannot be predicted. The lamellae belonging to the deep corneal layer, of both the donor and recipient, produce diffraction effects. In an intact cornea the organisation of the lamellae of the deep stromal layers is coherent and the effects of the perpendicular lamellae compensate for one another. Optically, some lamellae produce diffractive phenomena when light passes through, whereas the others behave as a polarizing filter able to annul the disturbing components, guaranteeing transparency of the system.

In the case of lamellar transplant, the flap transplanted, optically interacting with the receiver bed, may cause interference phenomena. Although the receiver bed and the donor corneal flap may be considered optically free from defects, coupling with sub-optimal orientation may reduce the capacity of the resulting optical system to transmit the incident light.

As already mentioned, in reality it has been observed that also penetrating transplants, where there is no interaction with the corneal tissue of the recipient, are affected by the orientation of the implant. It is hypothesised that the influence of the orientation in this type of transplant may depend on the position of the cruciate region with respect to the insertions of the oculomotor muscles and therefore an incorrect angular positioning of the flap to be grafted with respect to the physiologically ideal positions.

Figure 2:
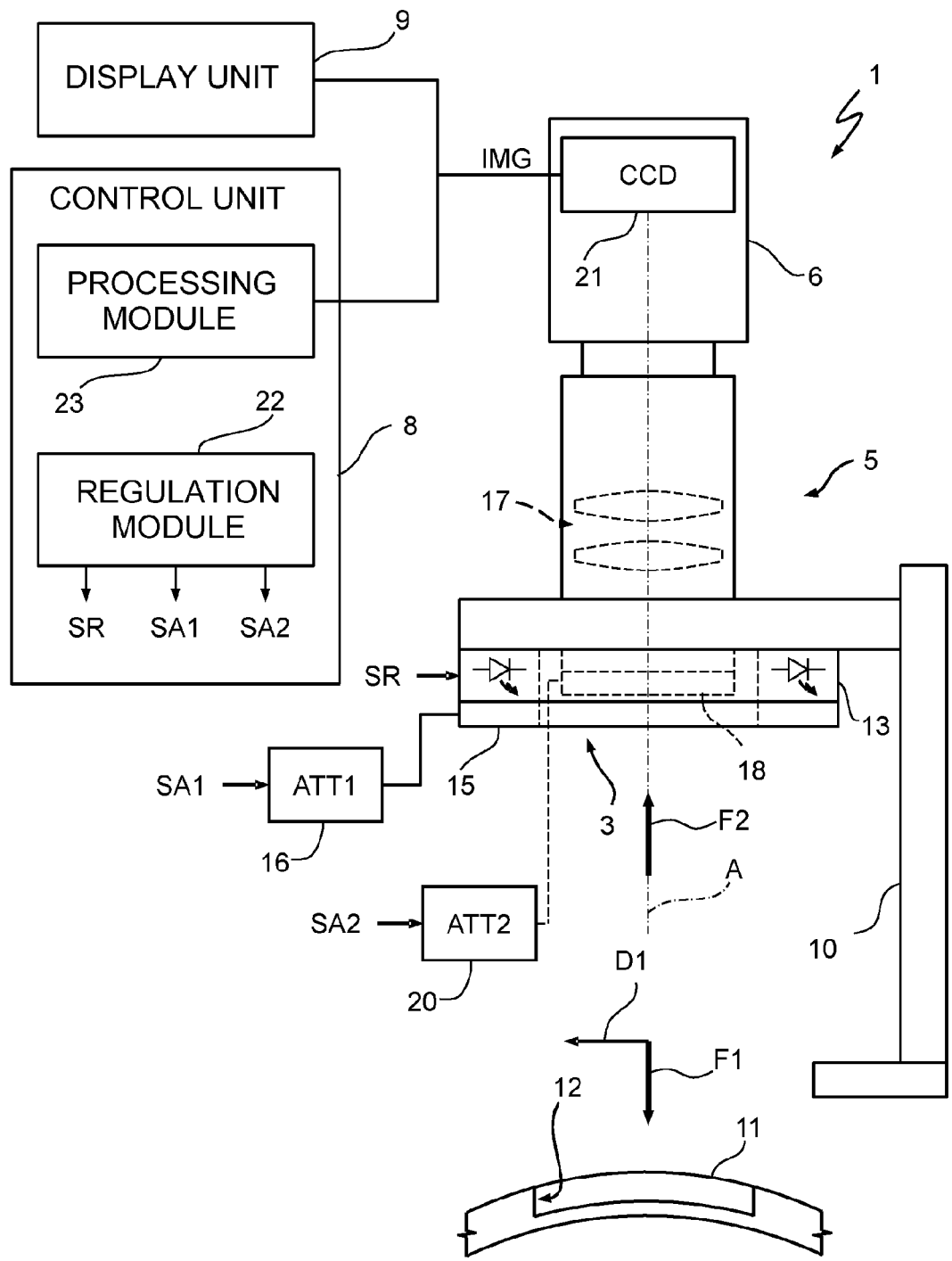
FIG. 2 shows a simplified block diagram of an apparatus for determining the orientation of anatomical cornea structures according to an embodiment of the present invention.
Figure 3:
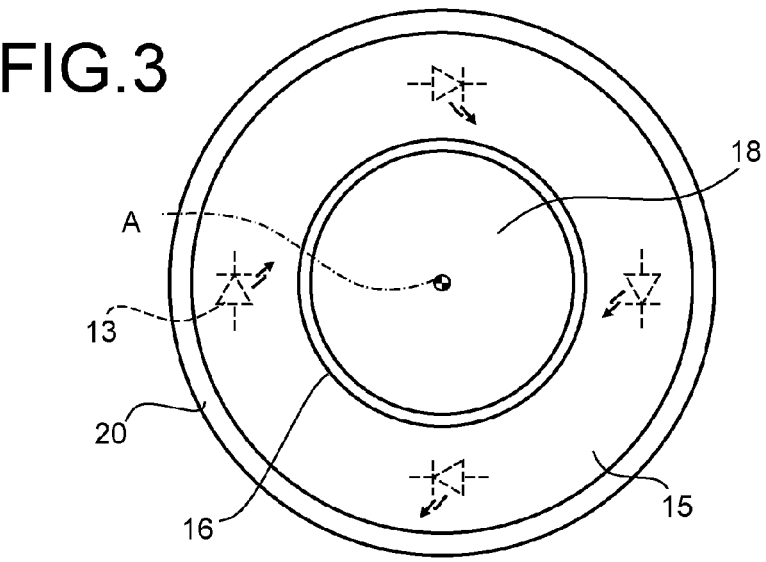
FIG. 3 is a view from below of a portion of the apparatus of FIG. 2.

With reference to FIGS. 2 and 3, an apparatus for determining the orientation of anatomical cornea structures is indicated as a whole by the number 1.

The apparatus 1 comprises an illumination device 3, an optical assembly 5, an image acquisition device 6, a control unit 8 and a display unit, for example a screen 9.

The illumination device 3, the optical assembly 5 and the image acquisition device 6 are mounted on a frame 10, which ensures correct alignment along an optical axis A. In particular, the frame 10 bears the illumination device 3 so that it is possible to illuminate a donor corneal flap 11 positioned in an observation seat 12, which may be a donor receiver bed, where the donor corneal flap 11 is deposited, or a support device, such as an artificial chamber (not shown here). Again, the subject of the observation can be a cornea in its original ocular structure, if the apparatus is used to determine the orientation of the native corneal tissue.

The optical assembly 5 and the image acquisition device 6 are fixed to the frame 10 so that it is possible to frame the donor corneal flap 11 in the observation seat 12.

The illumination device 3 comprises an annular light source 13, which is concentric to the optical assembly 5 and is therefore aligned with the optical axis A, and an emission polarizing filter 15 optically coupled with the light source 13. In one embodiment, the light source 13 is of the LED type and is driven by the control unit 8 through a regulation signal SR.

Like the light source 13, also the emission polarizing filter 15 has an annular shape and is arranged so as to intercept and polarize the luminous beam emitted from the light source 13. Therefore, the illumination device 3 provides a first luminous beam F1 of polarized light. Furthermore, the emission polarizing filter 15 is adjustable to select a polarization direction D1 of the first luminous beam F1. The polarization direction D1 of the first luminous beam F1 is therefore adjustable. In one embodiment, a first actuator 16 is coupled to the emission polarizing filter 15 and is controlled by the control unit 8 through a first actuation signal SA1 to rotate the emission polarizing filter 15 about the optical axis A. In this way, it is possible to vary the polarization direction D1 of the first luminous beam F1. The first actuator 16 may for example include a motorised ring nut (not illustrated in detail). In a different embodiment, the emission polarizing filter 15 can be manually adjusted.

The optical unit 5 comprises a focusing assembly 17 and an acquisition polarizing filter 18, which is provided with a second actuator 20.

The focusing assembly 17, illustrated only schematically in FIG. 2, comprises a lens assembly and allows focusing of a second luminous beam F2, coming from the donor corneal flap 11 accommodated in the observation seat 12 and illuminated by the first luminous beam F1, on an acquisition plane of the image acquisition device 6.

The acquisition polarizing filter 18 is arranged so as to intercept the second luminous beam F2 directed to the image acquisition device 6. Furthermore, the acquisition polarizing filter 18 is orientable about its own optical axis, which coincides with the optical axis A, independently of the orientation of the emission polarizing filter 15 and the polarization direction D1 of the first luminous beam F1. Since the second luminous beam F2 contains polarized luminous radiation, although with one or more polarization directions not necessarily coinciding with the polarization direction D1 of the first luminous beam F1, the intensity of the polarized components of the second luminous beam F2 can be selected by adjusting the orientation of the acquisition polarizing filter 18 with respect to the second incoming luminous beam F2.

The orientation of the acquisition polarizing filter 18 may be conveniently determined by the second actuator 20, which is controlled by the control unit 8 through a second actuation signal SA2.

The image acquisition device 6 is coupled to the optical assembly 5 so as to intercept at least a fraction of the second luminous beam F2, which is focused on an acquisition plane. In one embodiment, the image acquisition device 6 comprises for example a CCD image sensor 21 and supplies to the control unit 8 image signals IMG representing the donor corneal flap 11 positioned in the observation seat 12, for example in the form of brightness value matrices. In one embodiment, furthermore, acquisition of the images and production of the image signals IMG are controlled by the control unit 8.

In particular, the image signals IMG are formed from reception of the second focused luminous beam F2, which in turn is determined by the reflection and/or diffusion of the first luminous beam F1 due to the effect of the interaction with the structures at the back of the donor corneal flap 11. In particular, said structures at the back may include the patient's ocular structures (specifically iris and retina) in the case of corneal transplant or objective examination of the native corneal structure; or portions of a support device which acts as an observation seat.

The image signals IMG are displayed on the screen 9 and processed by the control unit 8 as described below.

The control unit 8 is configured to receive the image signals IMG from the image acquisition device 6 and to determine the orientation of the anatomical cornea structures of the donor corneal flap 11 in the observation seat 12.

In particular, the control unit 8 comprises a regulation module 22 and a processing module 23.

The regulation module 22 is configured to activate the first actuator 16 and the second actuator 20 so as to arrange the emission polarizing filter 15 and the acquisition polarizing filter 18 in succession in a plurality of angular positions around the optical axis A.

The processing module 23 requests from the image acquisition device 6 the image signals IMG corresponding to the angular positions assumed each time by the emission polarizing filter 15 and by the acquisition polarizing filter 18. Furthermore, the processing module 23 is configured to eliminate artefacts from the image signals IMG and to determine the orientation of the anatomical cornea structures of the donor corneal flap 11 in the observation seat 12, in cooperation with the regulation module 22.

Figure 4:
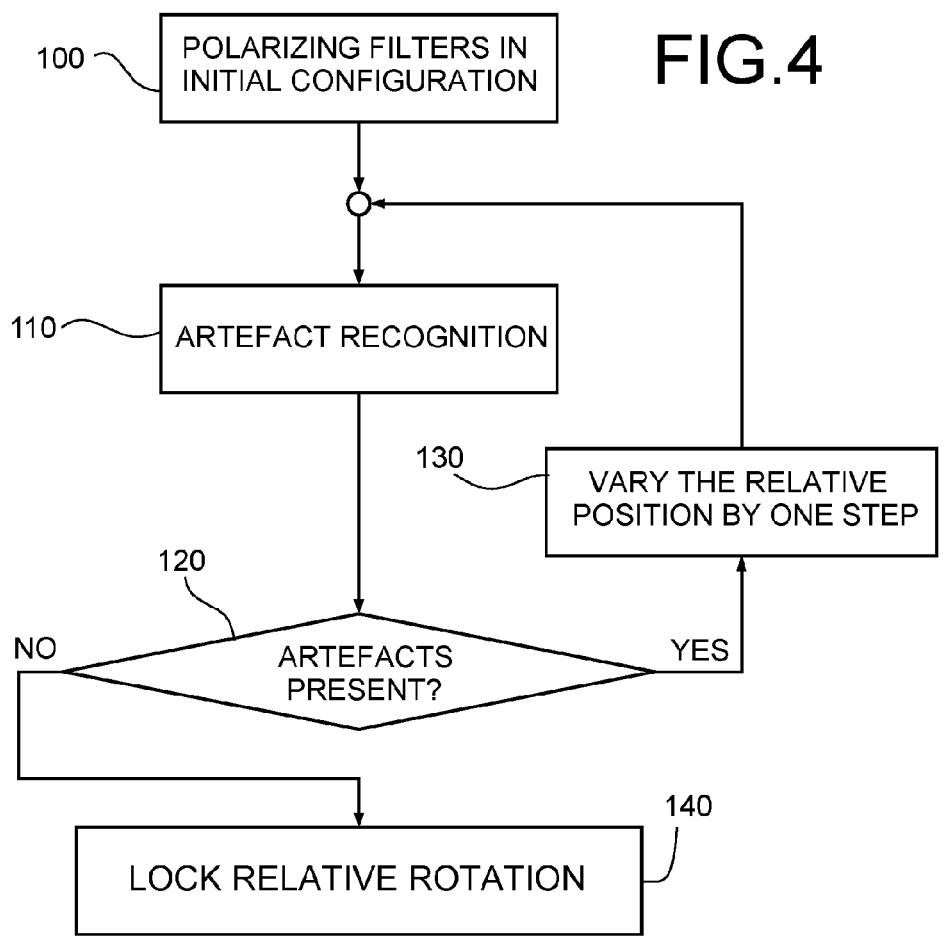
FIG. 4 is a flow diagram relative to phases of a method in accordance with an embodiment of the present invention.

Initially, the processing module 23 performs a procedure for eliminating the artefacts due to the reflection of the light source 13 on the surface of the donor corneal flap 11 (or also on the corneal surface of an eye), as shown in FIG. 4.

The procedure is based on the fact that the light coming from the light source 13 and striking the donor corneal flap (or from the entire cornea) 11 is polarized due to the effect of the emission polarizing filter 15, as well as the portion of light reflected from the donor corneal flap 11 contains polarized components (even though the polarization direction may not be the same). By modifying the relative angular position between the emission polarizing filter 15 and the acquisition polarizing filter 18, which may be oriented independently from each other thanks to the actuators 16, 20, it is possible to suppress the portion of polarized reflected light (in particular when the polarization direction of the acquisition polarizing filter 18 is perpendicular to the polarization direction of the portion of reflected light).

The processing module 23 controls the regulation module 22 so as to arrange the emission polarizing filter 15 and the acquisition polarizing filter 18 in an initial relative position (block 100) and performs a procedure for recognising the artefacts in the image signals IMG received (block 110). The recognition procedure is facilitated by the fact that the form and arrangement of the luminous elements of the light source 13 are known.

If artefacts are present (block 120, output SI), the regulation module 22, upon instruction of the processing module 23, acts on the first actuator 16 and/or on the second actuator 20 to vary by one step the current relative angular position of the emission polarizing filter 15 with respect to the acquisition polarizing filter 18 (block 130).

The phases of recognition of the artefacts (block 110) and of step variation of the current relative angular position (block 130) are repeated until the artefacts due to the reflection of the light source 13 are eliminated (block 120, output NO).

Once the artefacts have been removed, the relative rotation between the emission polarizing filter 15 and the acquisition polarizing filter 18 is locked, so that the emission polarizing filter 15 and the acquisition polarizing filter 18 are angularly fixed with respect to each other, although movable together (block 140). The locking of the relative rotation may be obtained either by driving in a coordinated manner the first actuator 16 and the second actuator 20 by means of the regulation module 22, or by a mechanical element, like a key. In practice, the regulation module 22 and the actuators 16, 20 prevent relative rotations between the emission polarizing filter 15 and the acquisition polarizing filter 18 in a first operative configuration; and allow relative rotations between the emission polarizing filter 15 and the acquisition polarizing filter 18 in a second operative configuration, in particular during the artefact cancellation procedure.

FIG. 5 illustrates a procedure for determining the orientation of the anatomical structures of the donor corneal flap 11 on the basis of the image signals IMG supplied by the image acquisition device 6. The procedure of FIG. 5 is preferably performed after the artefact elimination procedure of FIG. 4 and is based on the interaction of the first luminous beam F1 polarized with the anatomical cornea structures described with reference to FIG. 1 (in particular, the lamellae 52, 53 perpendicular to each other, which maintain a polarization direction, and the lamellae arranged along the arcs 55, which define the lobes 56 where the scattering effects are substantially isotropic).

The images corresponding to the lobes 56, due to the fact that the scattering is isotropic, are substantially independent of the orientation of the acquisition polarizing filter 18. On the contrary, the images corresponding to the cruciate region 57 are formed by polarized light and therefore can be acquired with maximum intensity only when the acquisition polarizing filter 18 is optically coupled with the lamellae 52, 53. The optical coupling occurs in four angular positions of the acquisition polarizing filter 18, corresponding to the directions of the lamellae 52, 53 (superoinferior and nasal-temporal) and spaced from each other by approximately 90°. Furthermore, also the arms of the cruciate region 57 are aligned in the superoinferior and nasal-temporal direction respectively.

To determine the orientation of the anatomical structures of the donor corneal flap 11, the processing module 23 controls the regulation module 22 so that the emission polarizing filter 15 and the acquisition polarizing filter 18 (block 200) perform a rotation of at least 90° and preferably 360°. More precisely, the emission polarizing filter 15 and the acquisition polarizing filter 18 are arranged in succession in a plurality of respective angular positions by the respective actuators 16, 20. In this phase, the relative angular position of the emission polarizing filter 15 and the acquisition polarizing filter 18 is maintained, which allows cancellation of the artefacts due to the reflection of the light emitted from the lighting device 3. Furthermore, the relative rotation between the emission polarizing filter 15 and acquisition polarizing filter 18 is prevented.

During the rotation of the emission polarizing filter 15 and the acquisition polarizing filter 18, the control unit 8 requests the image acquisition device 6 to acquire images at constant intervals and to provide corresponding image signals IMG to the processing module 23 (block 210).

The processing module 23 then begins the analysis of the image signals IMG acquired (block 220).

In detail, for each image signal IMG, the following operations are performed.

The processing module 23 extracts a circular image portion 30 (FIG. 6), corresponding to the donor corneal flap 11 (block 225).

Figure 6:
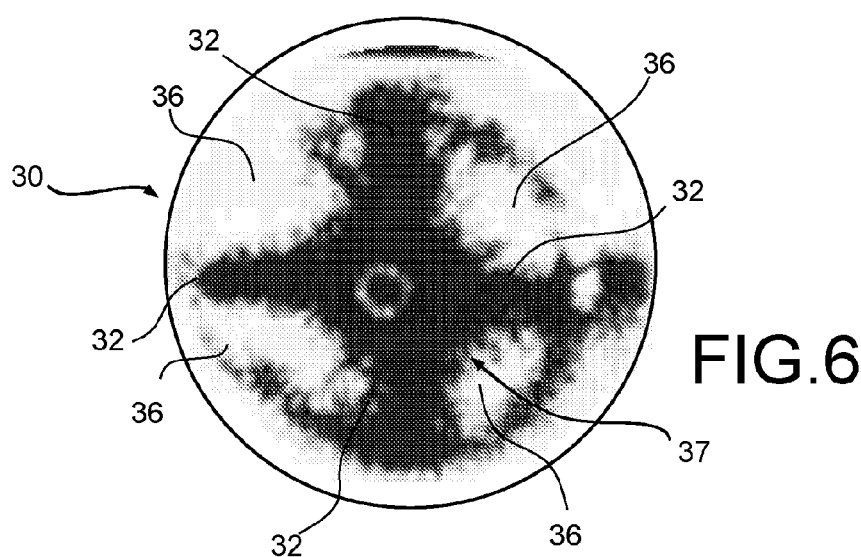
FIG. 6 is an example of an image of a cornea used in the device of FIG. 2.

The circular image portion 30 extracted is transformed into an image with two brightness levels (for example black and white) by means of point to point comparison with a brightness threshold (block 230; see also FIG. 6). For example, all the points of the original image that exceed the brightness threshold are assigned a first brightness value in the image transformed, while the image points that do not exceed the brightness value are assigned a second brightness value, distinct from the first brightness value. In a different embodiment, the circular image portion 30 can be converted into an image with several brightness levels.

Figure 7:
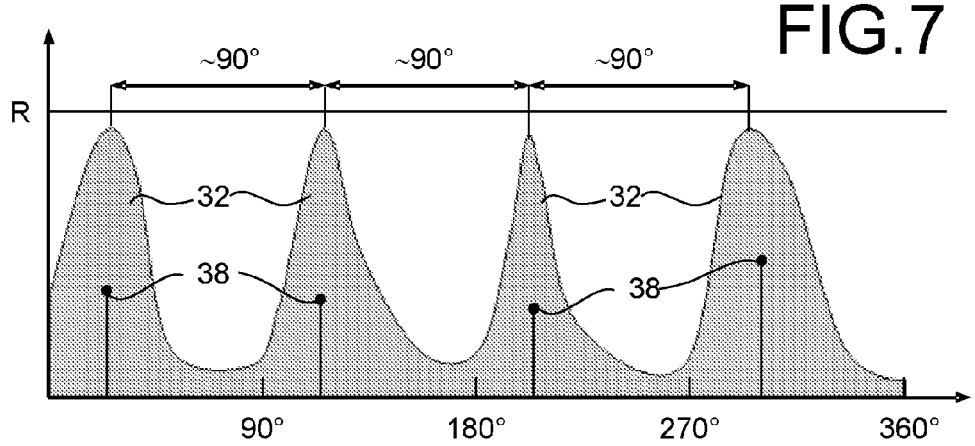
FIG. 7 is a transformed image obtained from the image of FIG. 6.

The processing module 23 then searches for and identifies portions of image 37 corresponding to the cruciate region 57, more precisely to its arms or ends. For this purpose, for example, the processing module 23 identifies a background brightness value (block 235) in image portions 36 corresponding to the lobes 56 (for example the first brightness value), and searches for the presence of candidate regions 32 with brightness value different from the background brightness value (for example the second brightness value) at the periphery of the circular image portion 30 (block 240). To identify the candidate regions 32, the circular image portion may be developed into a rectangular image 32 with base corresponding to the centre of the donor corneal flap 11 (FIG. 7). The processing module 23 then searches for and identifies candidate regions 32 which are continuous and have a different brightness value from the background brightness value, at a distance from the base of the rectangular image, i.e. at the periphery of the circular image portion 30. The barycentre 38 of the candidate regions 32 is determined and the angular position is identified. If three or four candidate regions 32 separated by angles of approximately 90° are identified (block 245 output YES), the candidate regions 32 are validated (block 250) and a partial recognition is considered successfully performed. The directions identified for the arms of the cruciate region 57 correspond to the superoinferior and nasal-temporal directions (primary) and provide a reference for the implant.

Alternatively, the search for the image portions corresponding to the arms of the cruciate region 57 may be conducted directly on the circular image portion 30, by analysing the brightness values of the points along circumferences of increasing radius.

Again alternatively, the processing module 23 may apply a Hough two-dimensional transform to the circular image portion and identify the presence and orientation of lines corresponding to the arms of the cruciate region 57.

If the number or the angular positions of the candidate regions 32 are not compatible (block 245 output NO), the candidate regions 32 are labelled as not validated (block 255).

The analysis phases of the image signals IMG (blocks 225-255) are repeated (block 260, output NO) until all the image signals IMG collected have been examined (block 260, output YES).

At the end of the procedure (block 270), calculation of the orientation of the arms of the cruciate region 57 may be refined, for example by determining the average orientation obtained from the image portions for which the partial recognition has been successful.

The apparatus according to the invention allows safe, rapid and reliable identification of the orientation of the anatomical structures of the donor corneal flap or, if necessary, of the native corneal tissue of a patient.

In particular, the orientation determined corresponds to the maximum light intensity value transmittable through the donor corneal flap 11 and guarantees the best implant conditions.

The implant, whether lamellar or penetrating, may therefore be performed so as to respect the orientation of the corneal lamellae of the donor and recipient, improving the probabilities of the patient's subjective visual perception corresponding to expectations.

The structure of the apparatus 1 is furthermore advantageously compact, thanks to the annular shape of the lighting device 3 and acquisition polarizing filter 15 and to mounting coaxial with the optical assembly 5 and with the image acquisition device 6.

Modifications and variations may be made to the apparatus and method described, without departing from the ambit of the present invention, as defined in the attached claims.

In particular, the phases of cancellation of the artefacts and identification of the cruciate structure 57 and its orientation can be performed, albeit not in such an accurate way, by an operator with the help of the image signals processed and displayed on the screen 9. Already the sole use of the polarizing filters 15, 18 described allows highlighting of the anatomical cornea structures, in particular the cruciate region 57, so that they can be seen also by the human eye. In practice, the orientation of the arms of the cruciate region 57 can be determined by the images displayed on the screen 9 using angular position references.

The invention claimed is:

1. An apparatus for determining the orientation of anatomical cornea structures, comprising:
    a lighting device configured to direct a first luminous radiation, polarized in an adjustable polarization direction, to a cornea, when the cornea is in an observation seat;
    an image acquisition device positioned to receive a second luminous radiation transmitted through the cornea arranged in the observation seat and illuminated by the first luminous radiation; and
    an acquisition polarizing filter positioned to intercept the second luminous radiation directed to the image acquisition device;
    wherein the acquisition polarizing filter is orientable and a fixed relative angular position of the acquisition polarizing filter with respect to the polarization direction is maintained during rotation at least in a first operative configuration.

2. An apparatus as claimed in claim 1, comprising a control device, configured to modify the polarization direction.

3. An apparatus as claimed in claim 1, wherein the lighting device comprises a light source; and an emission polarizing filter connected to the light source and orientable so as to maintain fixed a relative angular position with respect to the acquisition polarizing filter in the first operative configuration.

4. An apparatus as claimed in claim 3, wherein the acquisition polarizing filter is orientable independently of the polarization direction of the first luminous radiation in a second operative configuration.

5. An apparatus as claimed in claim 4, wherein the emission polarizing filter is orientable independently of the acquisition polarizing filter.

6. Apparatus according to claim 3, wherein the light source and the emission polarising filter have an annular shape and are coaxial with the acquisition polarizing filter.

7. Apparatus according to claim 3, comprising a first actuator and a second actuator coupled to the emission polarizing filter and to the acquisition polarizing filter respectively, and configured to adjust the relative angular position of the emission polarizing filter and the acquisition polarizing filter.

8. An apparatus as claimed in claim 3, comprising locking means activatable to prevent relative rotations between the emission polarizing filter and the acquisition polarizing filter in a first operative configuration, and to allow relative rotations between the emission polarizing filter and the acquisition polarizing filter in a second operative configuration.

9. An apparatus as claimed in claim 3, wherein the image acquisition device is configured to generate image signals from the second luminous radiation; and comprising a control unit configured to determine the orientation of anatomical structures of the cornea in the observation seat from the image signals.

10. An apparatus as claimed in claim 9, wherein the emission polarizing filter is orientable independently of the acquisition polarizing filter;
and wherein the control unit is configured to:
rotate the acquisition polarizing filter with respect to the emission polarizing filter in the second operative configuration;
rotate the emission polarizing filter and acquisition polarizing filter together along an arc of at least 90°, with no relative rotation of the emission polarizing filter and acquisition polarizing filter, in the first operative configuration;
request the image acquisition device to supply image signals corresponding to respective angular positions of the emission polarizing filter and acquisition polarizing filter in the second operative configuration;
receive the image signals generated by the image acquisition device;
determine a background brightness value;
search for candidate regions which are continuous and have a brightness value different from the background brightness value; and
determine respective angular positions of the candidate regions.

11. An apparatus as claimed in claim 10, wherein the control unit is configured to:
identify three or four candidate regions;
determine respective barycentres of the candidate regions; and
determine respective angular positions of the barycentres.

12. A method of determining the orientation of anatomical cornea structures, comprising:
directing a first luminous radiation, polarized in a polarization direction, to a cornea inside an observation seat;
modifying the polarization direction of the first luminous radiation;
acquiring images of the cornea arranged in the observation seat and illuminated by the first luminous radiation;
filtering, by an acquisition polarizing filter, a second luminous radiation transmitted through the cornea located inside the observation seat and illuminated by the first luminous radiation;
modifying an orientation of the acquisition polarizing filter and maintaining a fixed relative angular position of the acquisition polarizing filter with respect to the polarization direction.

13. A method as claimed in claim 12, comprising activating a light source and optically coupling the light source to an emission polarizing filter, the light source and the emission polarizing filter being concentric to the acquisition polarizing filter.

14. A method as claimed in claim 13, comprising orienting the emission polarizing filter independently of the acquisition polarizing filter before modifying the orientation of the acquisition polarizing filter.

15. A method as claimed in claim 13, comprising preventing relative rotations between the emission polarizing filter and the acquisition polarizing filter in a first operative configuration and allowing relative rotations between the emission polarizing filter and the acquisition polarizing filter in a second operative configuration.

16. A method as claimed in claim 12, comprising generating the images from the filtered second luminous radiation, and determining the orientation of anatomical structures of the cornea in the observation seat from the images.

17. A method as claimed in claim 16, wherein determining the orientation of anatomical structures of the cornea comprises:
rotating the polarization direction of the first luminous radiation and the acquisition polarizing filter together along an arc of at least 90°, with no relative rotation between the polarization direction of the first luminous radiation and the acquisition polarizing filter, in the first operative configuration.

18. A method as claimed in claim 17, wherein determining the orientation of anatomical structures of the cornea comprises: acquiring images corresponding to respective angular positions of the emission polarizing filter and of the acquisition polarizing filter in the second operative configuration.

19. A method as claimed in claim 18, wherein determining the orientation of anatomical cornea structures comprises:
determining a background brightness value of the images;
searching for continuous candidate regions having a brightness value different from the background brightness value;
validating the candidate regions; and
determining respective angular positions of the candidate regions.

20. A method as claimed in claim 19, wherein determining the orientation of anatomical structures of the cornea comprises:
determining respective barycentres of the candidate regions; and
determining respective angular positions of the barycentres.

21. A method as claimed in claim 19, wherein validating comprises identifying three or four candidate regions separated by roughly 90° angles in one of the images.

22. A method as claimed in claim 12, comprising:
using a light source to generate the first luminous radiation;
setting a current relative angular position of the acquisition polarizing filter with respect to the polarization direction of the first luminous radiation;
acquiring an image of the cornea in the observation seat in the current relative angular position;
searching for artefacts, produced by reflection of the light source, in the image acquired in the current relative angular position;
altering the current relative angular position, if artefacts are found;
preventing alteration of the current relative angular position, if no artefacts are found.

* * * * *